United States Patent
Tuller et al.

(10) Patent No.: US 6,627,959 B1
(45) Date of Patent: Sep. 30, 2003

(54) P-N JUNCTION SENSOR

(75) Inventors: Harry L. Tuller, Wellesley, MA (US); Richard Mlcak, Cambridge, MA (US)

(73) Assignee: Boston MicroSystems, Inc., Woburn, MA (US)

( * ) Notice: Subject to any disclaimer, the term of this patent is extended or adjusted under 35 U.S.C. 154(b) by 0 days.

(21) Appl. No.: 10/123,900

(22) Filed: Apr. 16, 2002

(51) Int. Cl.[7] .............................................. A01L 29/76
(52) U.S. Cl. ...................................................... 257/367
(58) Field of Search ................................ 257/367, 255, 257/414

(56) References Cited

U.S. PATENT DOCUMENTS

| | | | |
|---|---|---|---|
| 4,103,227 A | 7/1978 | Zemel | 324/65 |
| 4,302,530 A | 11/1981 | Zemel | 430/311 |
| 4,313,338 A | 2/1982 | Abe et al. | 73/23 |
| 4,644,380 A | 2/1987 | Zemel | 357/25 |
| 4,878,015 A | 10/1989 | Schmidt et al. | 324/71.5 |
| 4,897,628 A * | 1/1990 | Ippommatsu et al. | 338/34 |
| 5,372,785 A | 12/1994 | Johnson et al. | 422/90 |
| 5,434,442 A | 7/1995 | Lesk et al. | 257/367 |
| 5,520,789 A | 5/1996 | Takahashi et al. | 204/424 |
| 5,747,815 A | 5/1998 | Young et al. | 250/423 |
| 5,821,402 A | 10/1998 | Okajima et al. | 73/23.2 |
| 5,879,630 A | 3/1999 | Lescouzeres et al. | 422/82.02 |
| 6,077,350 A * | 6/2000 | Morton et al. | 118/58 |
| 6,111,280 A | 8/2000 | Gardner et al. | 257/253 |

FOREIGN PATENT DOCUMENTS

EP   0575628 A1 * 12/1993

* cited by examiner

*Primary Examiner*—Jasmine J B Clark
(74) *Attorney, Agent, or Firm*—Hamilton, Brook, Smith & Reynolds, P.C.

(57) ABSTRACT

A sensor including a p-n junction for subjecting under a reverse electrical bias. A conductive layer is formed across the p-n junction for providing an alternative conductive path across the p-n junction. The conductivity of the conductive layer in the presence of a selected substance in an atmosphere is different than in the absence of the selected substance, wherein the conductivity of the conductive layer is indicative of the presence or absence of the selected substance.

17 Claims, 4 Drawing Sheets

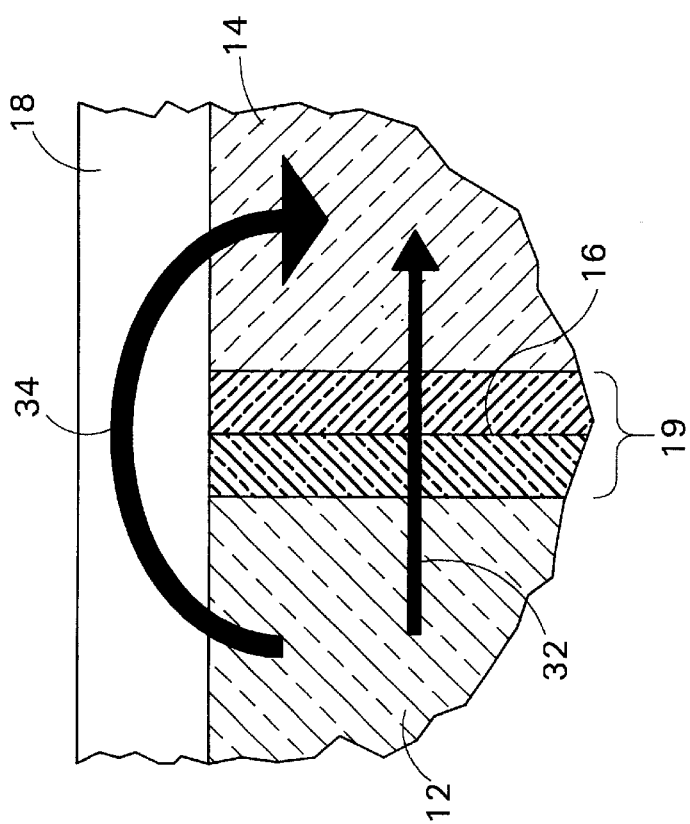
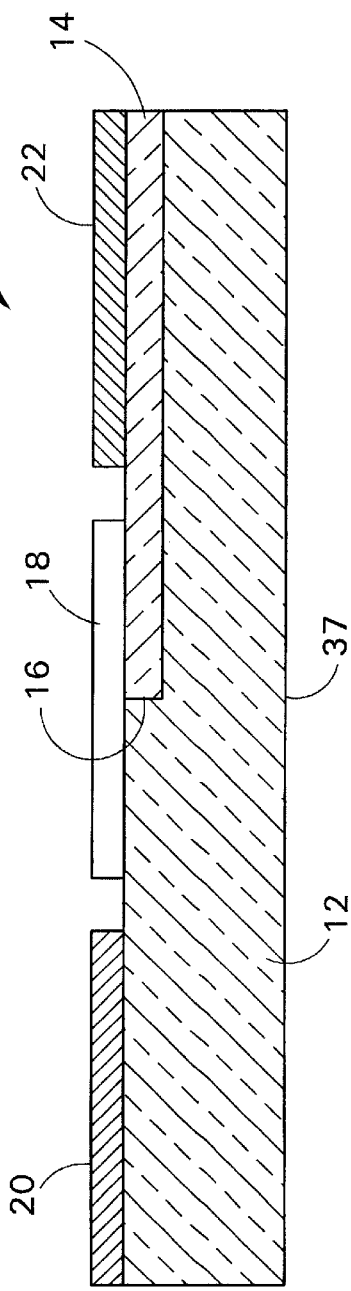

P-N JUNCTION SENSOR

BACKGROUND

In some situations, it is desirable to monitor emissions such as the exhaust from smoke stacks, engines, industrial processes, etc. to determine the presence and concentration of particular gases and/or aerosols. Sensors employed for such purposes are often subjected to harsh conditions, for example, high temperature and/or corrosive environments. However,.current commercially available gas sensors typically have designs which suffer from temperature limitations and are susceptible to corrosion. Consequently, these commercially available sensors are usually not suitable for use in such harsh environments. In addition, commercially available sensors often have further drawbacks, for example, sluggish response time, large sensor size, inconsistent quality and performance, performance degradation over time, high power requirements and high cost.

SUMMARY

The present invention provides a sensor for detecting the presence or absence of selected substances in an atmosphere such as gases, chemical species, aerosols, etc. Some embodiments of the present invention sensor can operate in high temperature and corrosive environments, can be small in size with low power requirements, can have a fast response time, can be low cost, and can be manufactured with consistent quality and provide consistent performance.

One embodiment of the present invention is a gas sensor which includes a p-n junction for subjecting under a reverse electrical bias. A gas sensitive conductive layer is formed across the p-n junction for providing an alternative conductive path across the p-n junction. The conductivity of the conductive layer in the presence of a selected gas is different than in the absence of the selected gas, wherein the conductivity of the conductive layer is indicative of the presence or absence of the selected gas.

In preferred embodiments, the conductive layer has a level of conductivity that vanes with varying concentrations of the selected gas such that the conductivity is indicative of the concentration of the selected gas. The conductive layer can be formed from inorganic, organic, or a composite of organic and inorganic materials. A voltage source is electrically connected to opposite sides of the p-n junction for providing the reverse electrical bias. A measurement device measures electrical properties across the conductive layer. The electrical properties can be any of current, resistance, capacitance and impedance. The p-n junction is formed from n-type and p-type semiconductor regions that are adjacent to each other. In one embodiment, one of the regions is formed within the other region. In another embodiment, one region is over the other region. In such an embodiment, at least one opening can extend through at least a portion of the n-type and p-type regions to expose the p-n junction within the opening. At least a portion of the conductive layer is disposed within the opening across the p-n junction. The conductive layer further extends over at least a portion of the n-type and p-type regions surrounding the at least one opening. In yet another embodiment, a cavity is formed below the n-type and p-type regions to thermally isolate the sensor from the substrate. A heating arrangement can be provided for heating the gas sensor.

The present invention also provides a sensor including a p-n junction for subjecting under a reverse electrical bias. A conductive layer is formed across the p-n junction for providing an alternative path across the p-n junction. The conductivity of the conductive layer in the presence of a selected substance in an atmosphere is different than in the absence of the selected substance, wherein the conductivity of the conductive layer is indicative of the presence or absence of the selected substance.

In preferred embodiments, the conductive layer has a level of conductivity that varies with varying concentrations of the selected substance such that the conductivity is indicative of the concentration of the selected substance. A voltage source is electrically connected to opposite sides of the p-n junction for providing the reverse electrical bias. A measurement device measures electrical properties across the conductive layer. The electrical properties are any of current, resistance, capacitance and impedance.

The present invention also provides a method of sensing a selected gas with a sensor including subjecting a p-n junction of the sensor under a reverse electrical bias. A gas sensitive conductive layer extends across the p-n junction for providing an alternative conductive path across the p-n junction. The conductivity of the conductive layer in the presence of the selected gas is different than in the absence of the selected gas. Electrical properties are measured across the conductive layer to determine the presence or absence of the selected gas.

In preferred embodiments, the conductive layer has a level of conductivity that varies with varying concentrations of the selected gas. The concentration of the selected gas is determined based on the level of conductivity of the conductive layer. Any of current, resistance, capacitance and impedance is measured across the conductive layer. In some embodiments, the sensor is heated with a heating arrangement to a desired operating temperature.

The present invention also provides a method of sensing a selected substance in an atmosphere with a sensor including subjecting a p-n junction of the sensor under a reverse electrical bias. A conductive layer extends across the p-n junction for providing an alternative conductive path across the p-n junction. The conductivity of the conductive layer in the presence of the selected substance in the atmosphere is different than in the absence of the selected substance. Electrical properties are measured across the conductive layer to determine the presence or absence of the selected substance.

In preferred embodiments, the conductive layer has a level of conductivity that varies with varying concentrations of the selected substance. The concentration of the selected substance is determined based on the level of conductivity of the conductive layer. Any one of current, resistance, capacitance and impedance is measured across the conductive layer. In some embodiments, the sensor is heated with a heating arrangement to a desired operating temperature.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3 is a schematic drawing depicting flow of current through the p-n junction and the gas sensitive layer.

FIG. 4 is a schematic drawing of another embodiment of the present invention.

DETAILED DESCRIPTION OF THE INVENTION

Figure 1:
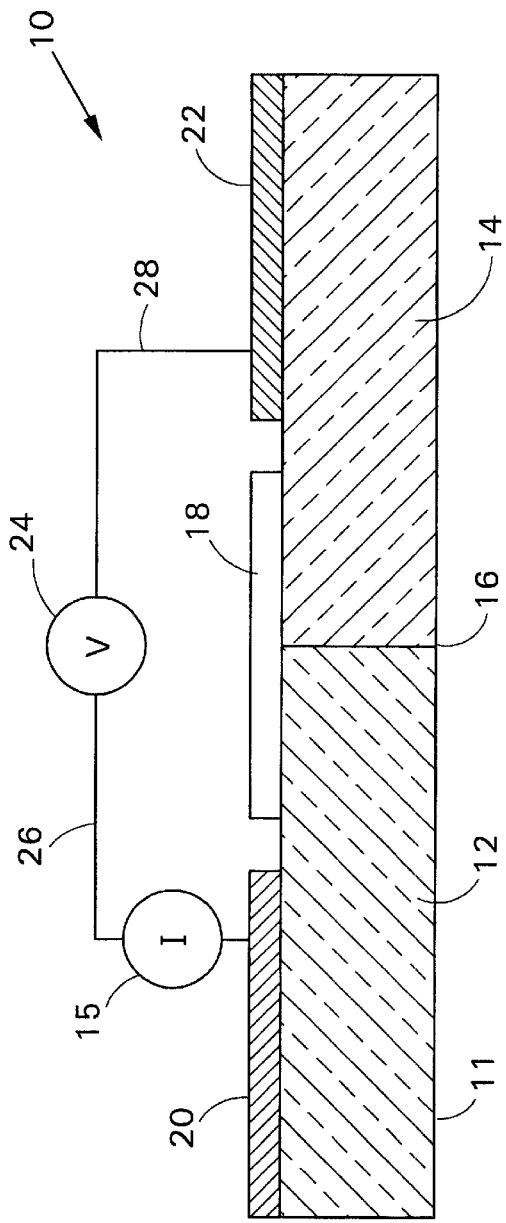
FIG. 1 is a schematic drawing of an embodiment of the present invention sensor.

Referring to FIG. 1, sensor 10 is capable of sensing the presence and/or concentration of selected substances within an atmosphere or environment, such as gases, chemical species, aerosols, etc. In many applications, sensor 10 is employed as a gas sensor. Sensor 10 includes a semiconductor substrate 11 having an n-type semiconductor region or layer 12 abutting a p-type semiconductor region or layer 14 with a p-n junction 16 therebetween. Ohmic contacts 20 and 22 are formed on the n-type region 12 and the p-type region 14, respectively. A voltage source 24 is electrically connected to the n-type region 12 and p-type region 14 via lines 26 and 28, which are connected to respective contacts 20 and 22. Voltage source 24 provides a reverse electrical bias across the p-n junction 16. A substance sensitive conductive layer 18 is formed over the substrate 11 and across an exposed region of the p-n junction 16 to provide an alternative conductive path past or across the p-n junction 16. The conductive layer 18 has a conductivity that varies depending upon the concentration of a particular substance, such as a gas or gases, chemical species, aerosols, etc., coming into contact with conductive layer 18, and thereby modulates the flow of current. A measurement device such as a current meter 15 measures the flow of current between contacts 20 and 22, thereby measuring the flow of current through conductive layer 18. The concentration and/or presence of the selected substance can be determined by the level of measured current.

Figure 2:
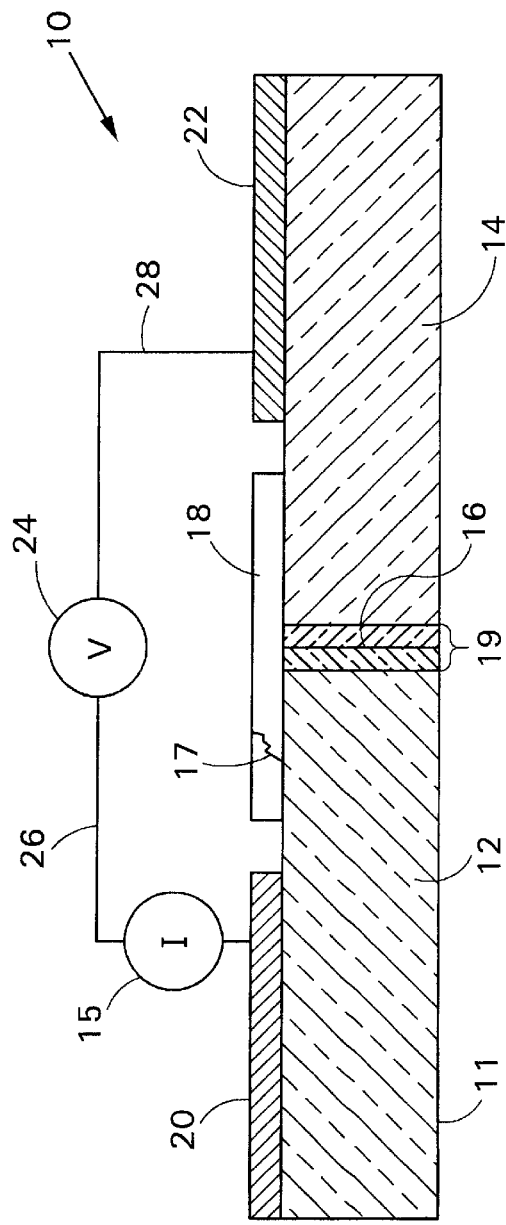
FIG. 2 shows the p-n junction depletion zone and a crack/defect in the gas sensitive layer in the embodiment of FIG. 1.

In operation, when voltage source 24 subjects the p-n junction 16 to a reverse electrical bias, very little p-n junction current 32 (FIG. 3) passes from the n-type region 12 to the p-type region 14 through the p-n junction 16. The p-n junction 16 has a very short or narrow space charge width or depletion zone 19 (FIGS. 2 and 3), typically 0.5 $\mu$m or less. Referring to FIG. 3, although very little p-n junction current 32 flows through the p-n junction 16, a parallel or bypass leakage shorting current 34 flows from the n-type region 12 to the p-type region 14 through conductive layer 18. The bypass current 34 only has to flow around the depletion zone 19 through conductive layer 18 to flow past or across the p-n junction 16. The conductivity of the conductive layer 18 varies depending upon the concentration of a selected substance coming into contact with conductive layer 18. The conductivity is affected by the absorption, desorption, or reaction of the substance at the exposed conductive layer 18. As a result, the material from which conductive layer 18 is formed, is chosen to respond to a specific substance or family of substances to be monitored. By measuring the current 1 passing between contacts 20/22 with current meter 15, the current 34 through conductive layer 18 is measured. Measurements of different currents 34 through conductive layer 18 are correlated to different concentrations as well as the presence and absence of the selected substance or substances. Typically, current levels are predetermined for particular concentrations. If needed, the p-n junction current 32 is accounted for. Also, each sensor 10 can be calibrated to account for variations occurring in the manufacturing process.

The very narrow depletion zone 19 (FIG. 3) of the p-n junction 16 around which the leaking shorting current 34 flows, allows the conductive layer 18 to be unaffected by most cracks or defects 17 (FIG. 2) in conductive layer 18. As seen in FIG. 3, the leaking shorting current 34 within conductive layer 18 can flow around the p-n junction 16 in close relationship thereto such that any cracks or defects 17 that are away from the p-n junction 16 have little effect on the flow of the leaking shorting current 34. Consequently, cracks and defects 17 can form in the conductive layer 18 during manufacturing and/or during use, and not affect the operation of sensor 10. Typically, only the cracks or defects 17 that are directly over the p-n junction 16 may possibly affect the performance of the sensor 10. Usually, such cracks or defects 17 would have to extend transverse to the flow of the leaking shorting current 34 to affect the flow of current 34. Since most cracks or defects 17 are typically short and would not extend the whole lateral distance across conductive layer 18 while directly over p-n junction, the leaking shorting current 34 is usually able to flow around the crack/defect 17. Cracks or defects 17 extending in the same direction as the leaking shorting current 34 might not affect the flow of current 34. If the cracks or defects 17 are formed during the manufacture of sensor 10, the sensor can be calibrated to compensate for any effects caused by the cracks or defects 17.

The n-type semiconductor region 12 and the p-type semiconductor region 14 can be made of silicon (Si) if sensor 10 operates in non-corrosive low temperature environments below temperatures of approximately 150° C. For higher operating temperatures, semiconductor materials with a large band gap are typically employed such as silicon carbide (SiC), gallium nitride (GaN), etc., where the particular materials are selected so that the operating temperature is below the temperature at which the semiconductor material becomes intrinsic, or so that the p-n junction reverse bias current 32 does not become too large. Silicon carbide is suitable for use in both high temperature and corrosive environments. The substrate 11 can in some embodiments be about 1 mm long by 1 mm to 10 mm wide with the n-type 12 and p-type regions 14 being about 0.5 microns to 0.5 mm thick. The n-type region 12 and the p-type region 14 can be formed by common methods such as diffusion, implantation or epitaxial growth, and can be formed onto a substrate such as silicon, silicon carbide, gallium nitride, gallium arsenide, or other semiconductors or materials onto which semiconductors can be formed. The contacts 20/22 are typically made of metals capable of forming stable low resistivity electrical contacts to the semiconductor materials of regions 12/14 and formed on regions 12/14 by sputtering, e-beam evaporation, pulsed laser deposition, electrochemical deposition or chemical vapor deposition.

The conductive layer 18 can be formed of either inorganic or organic materials. Since the leaking shorting current 34 only needs to pass through about 0.5 $\mu$m of conductive layer 18 in order to bypass the p-n junction 16, the conductive layer 18 can be at thicknesses below 1 micron such as 100 nm. At such thicknesses, conductive layer 18 is less susceptible to thermal/mechanical induced microcracking. Typically, conductive layer 18 is long and wide enough to completely cover the p-n junction depletion zone 19 and extend at least another 100 nm over regions 12/14 immediately adjacent to p-n junction depletion zone 19. Examples of inorganic materials for conductive layer 18 include semiconducting metal oxides such as tin oxide ($SnO_2$), zinc oxide (ZnO), titanium dioxide ($TiO_2$), gallium oxide ($Ga_2O_3$), indium oxide ($In_2O_3$), molybdenum oxide ($MoO_3$), tungsten oxide ($WO_3$), etc. Examples of organic materials. for conductive layer 18 include polymer films such as polypyrroles and polyanilinebased composites, self assembled monolayers, and immobilized antibodies and other biomolecular species. The conductive layer 18 can be formed by physical deposition process such as thermal, electron beam, molecular beam or pulsed laser evaporation, or sputtering. In addition, the conductive layer 18 can be formed by chemical deposition processes such as chemical vapor deposition, spin-on of organic precursors, oxidation, hybridization, etc. Furthermore, conductive layer 18 can be formed by depositing a film of the desired material over the entire substrate 11 and then lithographically patterning the film to remove the film from unwanted areas. The conductive layer 18 can also be formed by selective deposition such as sputtering through a mask or by thermal activated self lithographic chemical vapor deposition (CVD) directly onto heated regions.

The conductive layer 18 typically conducts a certain level of current in the absence of the selected substance or substances and then changes in the presence of the selected substance or substances. However, in some cases, near-zero current can be conducted for one condition and then various levels of current conducted in other conditions. Conductive layer 18 can be a single layer of a single material, or alternatively, be formed of more than one layer, as well as contain more than one material. When multiple layers form conductive layer 18, the layers can be of different materials. The conductive layer 18 can be formed to respond to a single substance or multiple substances. In addition; an array of conductive layers 18 formed of different materials can be employed for detecting multiple substances such as multiple gases. The array of conductive layers 18 can be formed by an array of multiple individual sensors 10, or can be formed by multiple conductive layers 18 formed on different p-n junctions 16 that are located on a single substrate. Although the level of current through conductive layer 18 is typically measured, alternatively, the magnitude of other electrical properties can be measured with the appropriate equipment such as resistance, capacitance and impedance.

Sensor 10 can be manufactured with relatively consistent quality and provide consistent performance over time. Consistent quality and performance are in part provided by having a very thin conductive layer 18 which is less susceptible to cracking. In addition, even when some cracking occurs, the effects of cracking are minimized by the fact that the leaking shorting current 34 only needs to pass through about 1 $\mu$m of the conductive layer 18. The simple design of sensor 10 also allows the sensor to be made small in size with low power requirements and relatively quick response time.

Referring to FIG. 4, sensor 36 is another embodiment of the present invention. Sensor 36 has a substrate 37 where the p-n junction 16 is formed by diffusing or implanting a p-type region 14 into a base substrate n-type region 12. The contacts 20/22 are then formed over the respective n-type and p-type regions 14 and the conductive layer 18 is formed over the exposed p-n junction 16. Alternatively, an n-type region 12 can be formed in a base substrate p-type region 14. In addition, formation of one of the n-type 12 or p-type regions 14 can be by epitaxial growth followed by selective removal of portions of the epitaxial layer by masking and etching processes.

Figure 5:
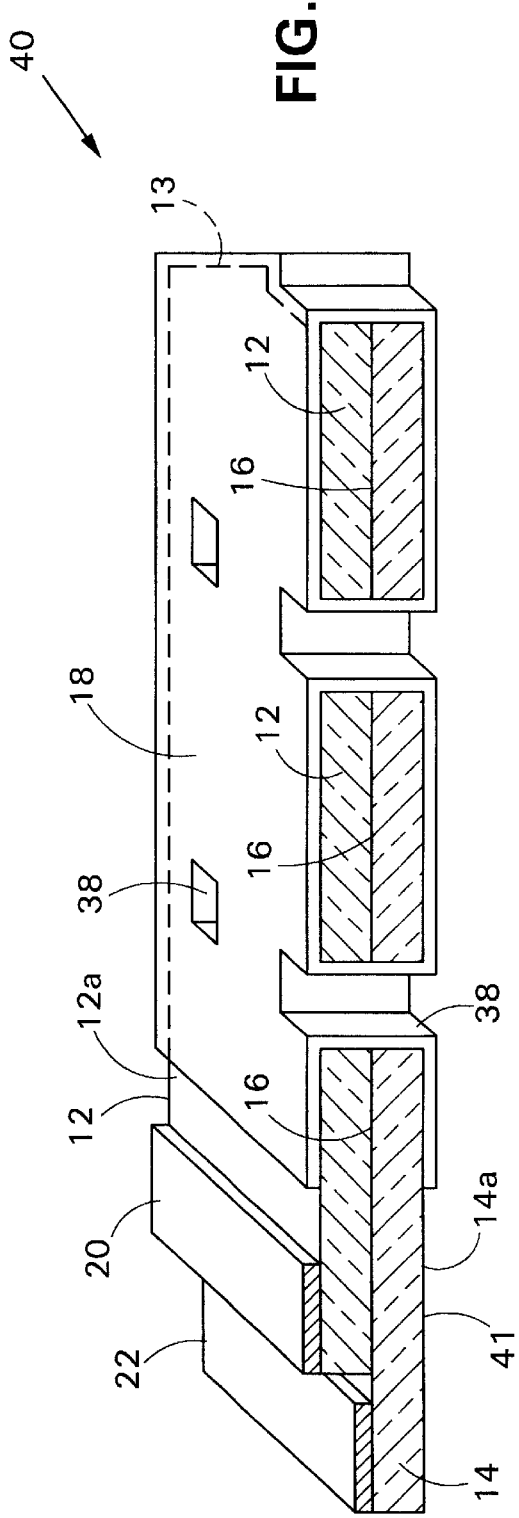
FIG. 5 is a perspective schematic drawing of yet another embodiment of the present invention.

Referring to FIG. 5, sensor 40 includes a substrate 41 with n-type 12 and p-type regions 14 that consist of abutting, adjacent or mating layers, one on top of another. The p-type region 14 is shown below the n-type region 12 and extends laterally beyond the n-type region 12 so that contacts 20 and 22 can be formed on respective n-type 12 and p-type regions 14. Voltage source 24 (FIG. 1) is electrically connected to contacts 20 and 22. A series of openings such as holes or apertures 38 extend through the n-type 12 and p-type regions 14 of substrate 41. The apertures 38 are shown to be square or rectangular and increase the exposed area of the p-n junction 16 to include the regions within the apertures 38 in addition to the existing perimeter of the mating n-type 12 and p-type regions 14. Conductive layer 18 is formed on selected portions of the substrate 41. The conductive layer 18 extends over a portion of the outwardly facing opposed planar surfaces 12a/14a and the outer perimeter 13 of the n-type 12 and p-type regions 14, as well as within the apertures 38, thereby extending over exposed regions of the p-n junction 16. Although the n-type region 12 is shown to be on top of the p-type region 14, alternatively, the orientation of the n-type 12 and p-type regions 14 can be reversed. In addition, the apertures 38 can be of other suitable shapes such as circular, oval, polygonal, or combinations thereof. The apertures 38 can also only extend through one of the n-type 12 or p-type 14 regions, thereby forming holes with closed ends to expose p-n junction 16 areas. In some cases, the apertures 38 can extend through one of the regions 12/14 and further extend partway through the other region. Furthermore, the size of the apertures 38 can be varied. For example, sensor 40 can have a single enlarged aperture 38 that forms a large central cavity. If desired, the contacts 20/22 can be at opposite ends of sensor 40.

Figure 6:
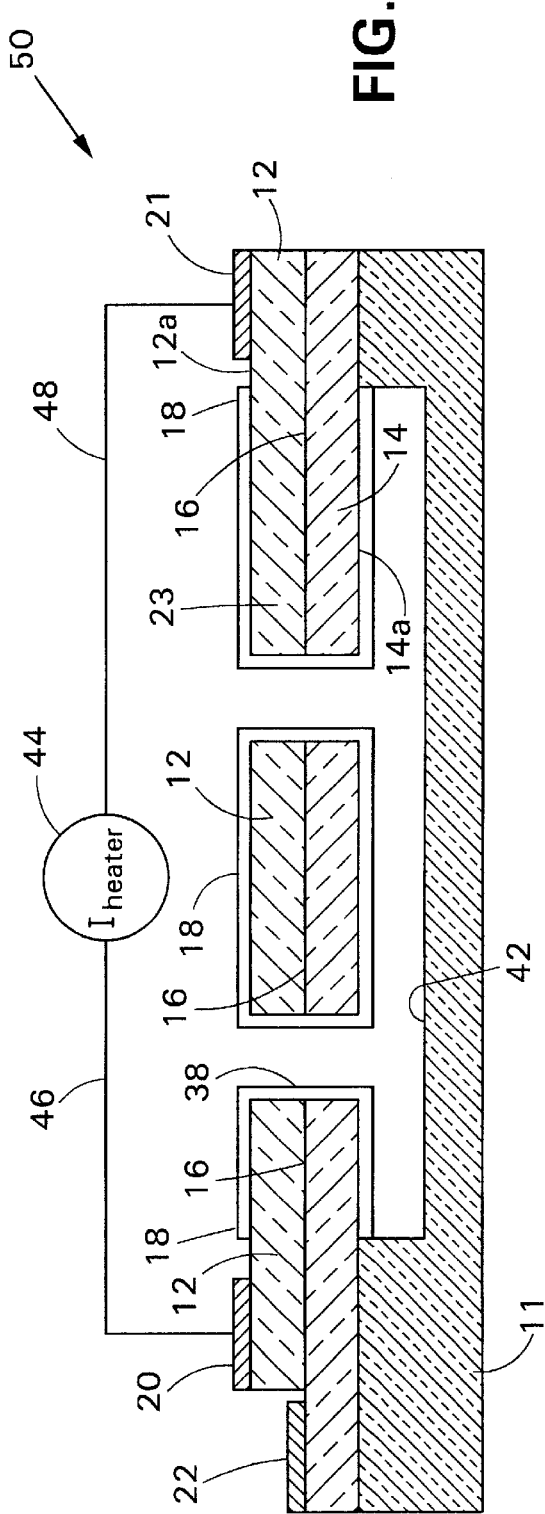
FIG. 6 is a schematic drawing of still another embodiment of the present invention.

Referring to FIG. 6, sensor 50 differs from sensor 40 in that sensor 50 includes a substrate 11 and underetched cavity 42 extending below the p-type region 14. The apertures 38 extend through the n-type region 12 and p-type layer 14 into cavity 42. Although the n-type region 12 is shown to be on top of the p-type region 14, alternatively, the orientation of the n-type region 12 and p-type regions 14 can be reversed. The apertures 38 can also only extend through one of the n-type 12 or p-type 14 regions, thereby forming holes with closed ends to expose p-n junction 16 areas. In some cases, the apertures 38 can extend through one of the regions 12/14 and further extend partway through the other region. Substrate 11 is formed from semiconductors such as silicon, silicon carbide, gallium nitride, gallium arsenide, or other semiconductors or materials in which cavity 42 can be precisely etched, and onto which n-type region 12 and the p-type region 14 can be formed.

The conductive layer 18 covers p-n junction 16, and may also cover all or part of n-type region 12 on top surface 12a, all or part of p-type region 14 on bottom surface 14a, all or part of aperture 38, and all or part of the surface of cavity 42. A portion of the n-type region 12, p-type layer 14, and conductive layer 18 forms an underetched structure 23. Voltage source 24 (FIG. 1) is electrically connected to contacts 20 and 22.

The n-type region 12 includes a second ohmic contact 21 on surface 12a. Contacts 20/21 are electrically connected to a heating power source 44 via lines 46 and 48. Current from power source 44 flows through n-type layer 12 and heats the n-type region 12, the p-type region 14 and the conductive layer 18 of the underetched structure 23 of sensor 50 to the desired operating temperature. This arrangement forms a microhotplate structure. Alternatively, second ohmic contact 21 can be formed on p-type layer 14 to heat underetched structure 23 by flowing current through p-type layer 14.

Heating the sensor 50 to a specified temperature can provide a more rapid response time, as well as optimum sensitivity and/or selectivity in responding to a particular substance over other substances in the atmosphere. Typical operating temperature ranges are 250° C. to 500° C. In example, heating can allow sensor 50 to distinguish between different gases by utilizing programmed heating cycles to obtain thermodynamic or kinetic information about the gases being measured. The heating can also accelerate sensor response by providing a more rapid indication of the presence and/or concentration of a particular selected gas. The heating can also be employed to burn off or evaporate condensed contaminants on surfaces of conductive layer 18 by periodically ramping sensor 50 to temperatures well above measurement temperatures. The cavity 42 reduces the thermal mass of the heated underetched structure 23 and also provides thermal isolation. As a result, the power required to heat the underetched structure 23 to the desired operating temperatures are several orders of magnitude below prior art sensors and can be as low as a few milliwatts. The underetched structure 23 also positions the heated portion of sensor 50 away from the electrical contacts 20, 21 and 22 so that the contacts 20, 21 and 22 can remain at ambient temperatures. This reduces or prevents drift in sensor response and/or the failure of contacts 20, 21 and 22. Such problems commonly occur to contacts that become heated to an elevated operating temperature. Although underetched structure 23 is generally shown as a micromechanical membrane structure, in other embodiments, different micromechanical structures can be formed such as cantilevered beams, microbridges, tethered microhotplates, membranes, etc. In some embodiments, cavities such as cavity 42 may have portions which extend to the perimeter of the sensor.

Figure 7:
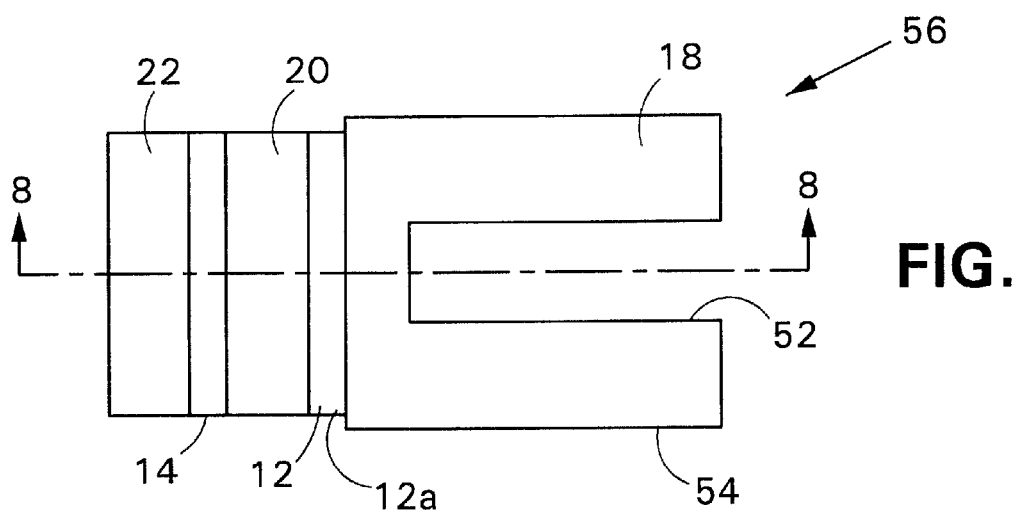
FIG. 7 is a plan schematic view of another embodiment of the present invention.
Figure 8:
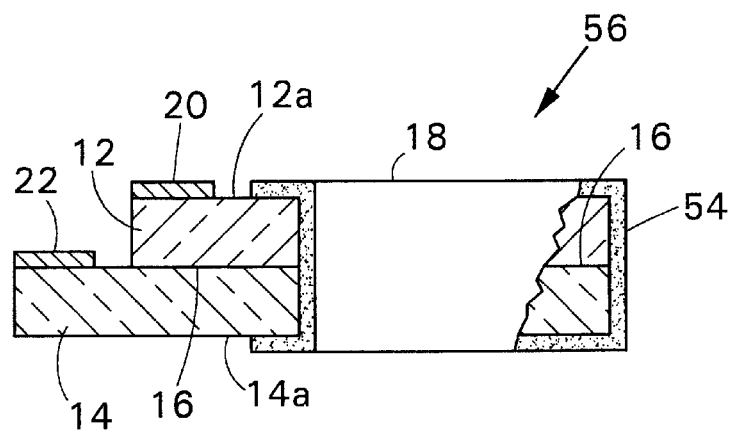
FIG. 8 is a sectional view of the embodiment depicted in FIG. 7 taken along lines 8—8 with a portion of the gas sensitive layer broken away to show part of the p-n junction.

Referring to FIGS. 7 and 8, sensor 56 differs from sensor 40 in that sensor 56 has patterned opening 52 extending through the n-type 12 and p-type regions 14 that is a slot instead of apertures 38 to expose increased areas of the p-n junction 16. The conductive layer 18 extends over the inner surfaces of the slot-like opening 52 and over the additional exposed p-n junction 16 areas. The slot-like opening 52 provides a lengthened exposed p-n junction 16 perimeter, and if desired, sensor 56 can include two or more slot-like openings 52 to further increase the exposed p-n junction 16. Although slot-like opening 52 is shown to have straight edges, alternatively opening 52 can have curved edges or be a convoluted pattern. In addition, the slot-like opening 52 does not have to extend completely through both the n-type 12 and p-type regions 14 to expose p-n junction 16 region.

Figure 9:
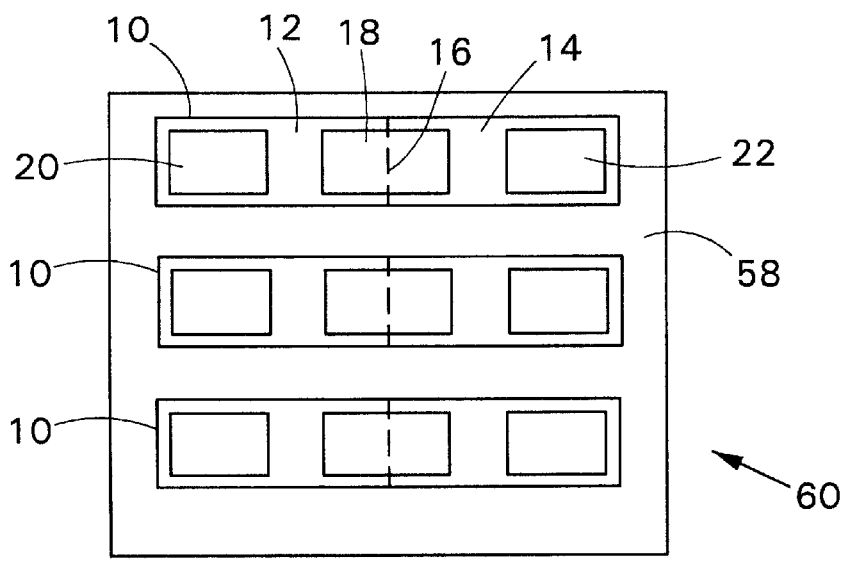
FIG. 9 is a plan schematic drawing of an array of present invention sensors formed on a substrate.

Referring to FIG. 9, sensor 60 includes a series or array of sensors 10 that are formed onto a substrate 58. The conductive layer 18 of each sensor 10 is chosen to detect the concentration and/or presence of particular selected substances. For example, each sensor 10 can be selected to detect a different gas. Consequently, by forming the array of sensors 10, a spectrum or range of gases can be detected. Although sensor 60 is depicted to have an array of sensors 10, it is understood that sensor 60 can have an array of any of the sensors of the present invention. It is also understood that the sensors can be positioned at any suitable orientation relative to each other.

While this invention has been particularly shown and described with references to preferred embodiments thereof, it will be understood by those skilled in the art that various changes in form and details may be made therein without departing from the scope of the invention encompassed by the appended claims.

For example, although the sensors of the present invention have been shown to be oriented horizontally, it is understood that in use, the orientation can be vertical or at any angle. In addition, it is understood that various features of the sensors in the present invention can be combined or omitted. Although the present invention is often employed for detecting gases, the present invention can also be used to detect aerosols (both suspended liquids and particles) and chemical species within particular atmospheres or environments. The aerosols can include biological agents such as simple organisms, bacteria and viruses. Also, the locations of positions of the n-type 12 and p-type regions 14 shown in the figures can be exchanged. An exposed p-n junction may be part of a number of devices which utilize p-n junctions in their design such as bipolar or JFET transistors (p-n-p or n-p-n), photo-diode light detectors, thyristors (p-n-p-n), etc. The operating characteristics of these devices can be modified by the existence of the conductive film which coats the exposed p-n junction or junctions. Vapors or chemical species can modify the conductivity of the conductive film which in turn can be detected by monitoring the changes in operation of the given devices, for example, a decrease in efficiency of a photo detector. The p-n junction does not need to be a homojunction (composed of the same material in both p and n regions), but can be a heterojunction such as p-SiC and n-GaN. Also, the substrate material need not be the same material as that of the p regions and n regions. Furthermore, any high impedance junction or junctions can be "shorted" by the conductive layer including metal-semiconductor schottky barriers or p-i-n (i-intrinsic or insulating region) junction structures used for photodetectors.

What is claimed is:

1. A gas sensor comprising:
    a p-n junction for subjecting under a reverse electrical bias; and
    a gas sensitive conductive layer formed across the p-n junction for providing an alternative conductive path across the p-n junction, the conductivity of the conductive layer in the presence of a selected gas being different than in the absence of the selected gas, wherein the conductivity of the conductive layer is indicative of the presence or absence of the selected gas.

2. The gas sensor of claim 1 in which the conductive layer has a level of conductivity that varies with varying concentrations of the selected gas such that the conductivity is indicative of the concentration of the selected gas.

3. The gas sensor of claim 1 further comprising a voltage source electrically connected to opposite sides of the p-n junction for providing the reverse electrical bias.

4. The gas sensor of claim 1 further comprising a measurement device for measuring electrical properties across the conductive layer, the electrical properties being any of current, resistance, capacitance and impedance.

5. The gas sensor of claim 1 in which the conductive layer is formed from inorganic, organic, or a composite of inorganic and organic materials.

6. The gas sensor of claim 1 in which the p-n junction is formed from n-type and p-type semiconductor regions that are adjacent to each other.

7. The gas sensor of claim 6 in which one of the regions is formed within the other region.

8. The gas sensor of claim 6 in which one region is over the other region, at least one opening extends through at least a portion of the n-type and p-type regions to expose the p-n junction within the opening, and at least a portion of the conductive layer is disposed within said opening across the p-n junction.

9. The gas sensor of claim 8 in which the conductive layer further extends over at least a portion of the n-type and p-type regions surrounding the at least one opening.

10. The gas sensor of claim 9 in which a cavity is formed below the n-type and p-type regions to thermally isolate the sensor from the substrate.

11. The gas sensor of claim 10 further comprising a heating arrangement for heating the gas sensor.

12. A gas sensor comprising:
- a p-n junction;
- a voltage source electrically connected to opposite sides of the p-n junction for subjecting the p-n junction under a reverse electrical bias;
- a gas sensitive conductive layer formed across the p-n junction for providing an alternative conductive path across the p-n junction, the conductivity of the conductive layer in the presence of a selected gas being different than in the absence of the selected gas; and
- measurement device for measuring current through the conductive layer, the amount of current being indicative of the presence or absence of the selected gas.

13. The gas sensor of claim 12 in which the conductive layer has a level of conductivity that varies with varying concentrations of the selected gas such that a particular level of current through the conductive layer is indicative of the concentration of the selected gas.

14. A sensor comprising:
- a p-n junction for subjecting under a reverse electrical bias; and
- a conductive layer formed across the p-n junction for providing an alternative conductive path across p-n junction, the conductivity of the conductive layer in the presence of a selected substance in an atmosphere being different than in the absence of the selected substance, wherein the conductivity of the conductive layer is indicative of the presence or absence of the selected substance.

15. The sensor of claim 14 in which the conductive layer has a level of conductivity that varies with varying concentrations of the selected substance such that the conductivity is indicative of the concentration of the selected substance.

16. The sensor of claim 14 further comprising a voltage source electrically connected to opposite sides of the p-n junction for providing the reverse electrical bias.

17. The sensor of claim 14 further comprising a measurement device for measuring electrical properties across the conductive layer, the electrical properties being any of current, resistance, capacitance and impedance.

* * * * *